(12) United States Patent
Foo et al.

(10) Patent No.: US 7,880,028 B2
(45) Date of Patent: *Feb. 1, 2011

(54) PROCESS FOR MAKING 3-PENTENENITRILE BY HYDROCYANATION OF BUTADIENE

(75) Inventors: Thomas Foo, Wilmington, DE (US); Sigridur S. Kristjansdottir, Wilmington, DE (US); Ronald J. McKinney, Wilmington, DE (US); Ron Ozer, Wilmington, DE (US); Paul S. Pearlman, Thornton, PA (US)

(73) Assignee: Invista North America S.A R.L., Wilmington, DE (US)

( * ) Notice: Subject to any disclaimer, the term of this patent is extended or adjusted under 35 U.S.C. 154(b) by 370 days.

This patent is subject to a terminal disclaimer.

(21) Appl. No.: 11/776,932

(22) Filed: Jul. 12, 2007

(65) Prior Publication Data

US 2008/0015380 A1 Jan. 17, 2008

Related U.S. Application Data

(60) Provisional application No. 60/830,970, filed on Jul. 14, 2006.

(51) Int. Cl.
*C07C 253/10* (2006.01)

(52) U.S. Cl. ........................ 558/338; 558/335

(58) Field of Classification Search .............. None
See application file for complete search history.

(56) References Cited

U.S. PATENT DOCUMENTS

| | | |
|---|---|---|
| 2,768,132 A | 10/1956 | Halliwell |
| 3,370,082 A | 2/1968 | Eisfeld et al. |
| 3,496,215 A | 2/1970 | Drinkard et al. |
| 3,496,217 A | 2/1970 | Drinkard, Jr. et al. |
| 3,496,218 A | 2/1970 | Drinkard, Jr. |
| 3,522,288 A | 7/1970 | Drinkard, Jr. et al. |
| 3,536,748 A | 10/1970 | Drinkard, Jr. et al. |
| 3,551,474 A | 12/1970 | Drinkard et al. |
| 3,564,040 A | 2/1971 | Downing et al. |
| 3,579,560 A | 5/1971 | Drinkard et al. |
| 3,655,723 A | 4/1972 | Drinkard, Jr. |
| 3,694,485 A | 9/1972 | Drinkard, Jr. et al. |
| 3,752,839 A | 8/1973 | Drinkard, Jr. et al. |
| 3,766,231 A | 10/1973 | Gosser et al. |
| 3,766,237 A | 10/1973 | Chia et al. |
| 3,766,241 A | 10/1973 | Drinkard, Jr. et al. |
| 3,773,809 A | 11/1973 | Walter |
| 3,775,461 A | 11/1973 | Drinkard, Jr. et al. |
| 3,798,256 A | 3/1974 | King et al. |
| 3,818,067 A | 6/1974 | Downing et al. |
| 3,818,068 A | 6/1974 | Wells |
| 3,846,474 A | 11/1974 | Mok |
| 3,849,472 A | 11/1974 | Waddan |
| 3,850,973 A | 11/1974 | Seidel et al. |
| 3,853,754 A | 12/1974 | Gosser |
| 3,853,948 A | 12/1974 | Drinkard, Jr. et al. |
| 3,864,380 A | 2/1975 | King et al. |
| 3,869,501 A | 3/1975 | Waddan |
| 3,903,120 A | 9/1975 | Shook, Jr. et al. |
| 3,920,721 A | 11/1975 | Gosser |
| 3,927,056 A | 12/1975 | Gosser |
| 3,947,487 A | 3/1976 | Crooks |
| 4,045,495 A | 8/1977 | Nazarenko et al. |
| 4,046,815 A | 9/1977 | Nazarenko |
| 4,076,756 A | 2/1978 | Nazarenko et al. |
| 4,087,452 A | 5/1978 | Kuntz |
| 4,146,555 A | 3/1979 | Kershaw |
| 4,147,717 A | 4/1979 | Kershaw |
| 4,177,215 A | 12/1979 | Seidel |
| 4,210,558 A | 7/1980 | Crooks |
| 4,230,634 A | 10/1980 | Benzie et al. |
| 4,240,976 A | 12/1980 | Benzie et al. |
| 4,251,468 A | 2/1981 | Nazarenko |
| 4,298,546 A | 11/1981 | McGill |
| 4,328,172 A | 5/1982 | Rapoport |
| 4,330,483 A | 5/1982 | Rapoport |
| 4,339,395 A | 7/1982 | Barnette et al. |
| 4,371,474 A | 2/1983 | Rapoport |
| 4,382,038 A | 5/1983 | McGill |
| 4,385,007 A | 5/1983 | Shook, Jr. |
| 4,416,824 A | 11/1983 | Reimer et al. |

(Continued)

FOREIGN PATENT DOCUMENTS

| | | |
|---|---|---|
| AU | 6522096 | 2/1997 |

(Continued)

*Primary Examiner*—Fiona T Powers
(74) *Attorney, Agent, or Firm*—Robert B. Furr, Jr.; Edward F. Kenchan, Jr.

(57) ABSTRACT

The invention provides a continuous process for the production of 3-pentenenitrile, comprising:
(a) contacting, in a reaction zone, a hydrogen cyanide-containing feed, a 1,3-butadiene-containing feed, and a catalyst precursor composition, wherein the catalyst precursor composition comprises a zero-valent nickel and at least one multidentate phosphorus-containing ligand selected from the group consisting of a phosphite, a phosphonite, a phosphinite, a phosphine, and a mixed phosphorus-containing ligand or a combination of such members; and
(b) maintaining a residence time sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture.

19 Claims, No Drawings

U.S. PATENT DOCUMENTS

| | | | |
|---|---|---|---|
| 4,416,825 A | 11/1983 | Ostermaier | |
| 4,434,316 A | 2/1984 | Barnette | |
| 4,539,302 A | 9/1985 | Leyendecker et al. | |
| 4,705,881 A | 11/1987 | Rapoport | |
| 4,749,801 A | 6/1988 | Bealty et al. | |
| 4,774,353 A | 9/1988 | Hall et al. | |
| 4,874,884 A | 10/1989 | McKinney et al. | |
| 4,990,645 A | 2/1991 | Back et al. | |
| 5,107,012 A | 4/1992 | Grunewald | |
| 5,302,756 A | 4/1994 | McKinney | |
| 5,312,959 A | 5/1994 | Sieja et al. | |
| 5,449,807 A | 9/1995 | Druliner | |
| 5,488,129 A | 1/1996 | Huser et al. | |
| 5,512,695 A | 4/1996 | Kreutzer et al. | |
| 5,512,696 A | 4/1996 | Kreutzer et al. | |
| 5,523,453 A | 6/1996 | Breikss | |
| 5,543,536 A | 8/1996 | Tam | |
| 5,663,369 A | 9/1997 | Kreutzer et al. | |
| 5,688,986 A | 11/1997 | Tam et al. | |
| 5,693,843 A | 12/1997 | Breikss et al. | |
| 5,696,280 A | 12/1997 | Shapiro | |
| 5,709,841 A | 1/1998 | Reimer | |
| 5,723,641 A | 3/1998 | Tam et al. | |
| 5,773,637 A | 6/1998 | Cicha et al. | |
| 5,821,378 A | 10/1998 | Foo et al. | |
| 5,847,191 A | 12/1998 | Bunel et al. | |
| 5,856,555 A | 1/1999 | Huser et al. | |
| 5,908,805 A | 6/1999 | Huser et al. | |
| 5,959,135 A | 9/1999 | Garner et al. | |
| 5,981,722 A | 11/1999 | Chen et al. | |
| 6,020,516 A | 2/2000 | Foo et al. | |
| 6,069,267 A | 5/2000 | Tam | |
| 6,090,987 A | 7/2000 | Billig et al. | |
| 6,121,184 A | 9/2000 | Druliner et al. | |
| 6,127,567 A | 10/2000 | Garner et al. | |
| 6,147,247 A | 11/2000 | Voit et al. | |
| 6,169,198 B1 | 1/2001 | Fischer et al. | |
| 6,171,996 B1 | 1/2001 | Garner et al. | |
| 6,171,997 B1 | 1/2001 | Foo et al. | |
| 6,197,992 B1 | 3/2001 | Fischer et al. | |
| 6,242,633 B1 | 6/2001 | Fischer et al. | |
| 6,284,865 B1 | 9/2001 | Tam et al. | |
| 6,307,109 B1 | 10/2001 | Kanel et al. | |
| 6,355,833 B2 | 3/2002 | Fischer et al. | |
| 6,461,481 B1 | 10/2002 | Barnette et al. | |
| 6,469,194 B2 | 10/2002 | Burattin et al. | |
| 6,521,778 B1 | 2/2003 | Fischer et al. | |
| 6,646,148 B1 * | 11/2003 | Kreutzer et al. | 558/78 |
| 6,660,877 B2 | 12/2003 | Lenges et al. | |
| 6,737,539 B2 | 5/2004 | Lenges et al. | |
| 6,753,440 B2 | 6/2004 | Druliner et al. | |
| 6,770,770 B1 | 8/2004 | Baumann et al. | |
| 6,846,945 B2 | 1/2005 | Lenges et al. | |
| 6,852,199 B2 | 2/2005 | Jungkamp et al. | |
| 6,855,799 B2 | 2/2005 | Tam et al. | |
| 6,893,996 B2 | 5/2005 | Chu et al. | |
| 6,897,329 B2 | 5/2005 | Jackson et al. | |
| 6,924,345 B2 | 8/2005 | Gagne et al. | |
| 6,936,171 B2 | 8/2005 | Jackson et al. | |
| 6,984,604 B2 | 1/2006 | Cobb et al. | |
| 7,022,866 B2 | 4/2006 | Bartsch et al. | |
| 7,067,685 B2 | 6/2006 | Bartsch et al. | |
| 7,084,293 B2 | 8/2006 | Rosier et al. | |
| 7,084,294 B2 | 8/2006 | Jungkamp et al. | |
| 7,098,358 B2 | 8/2006 | Burattin et al. | |
| 7,105,696 B2 | 9/2006 | Burattin et al. | |
| 7,253,298 B2 | 8/2007 | Galland et al. | |
| 7,345,006 B2 | 3/2008 | Bartsch et al. | |
| 7,381,845 B2 | 6/2008 | Weiskopf et al. | |
| 7,439,381 B2 | 10/2008 | Jungkamp et al. | |
| 7,442,825 B2 | 10/2008 | Galland et al. | |
| 7,470,805 B2 | 12/2008 | Rosier et al. | |
| 7,521,575 B2 | 4/2009 | Bartsch et al. | |
| 7,528,275 B2 | 5/2009 | Bartsch et al. | |
| 7,538,240 B2 * | 5/2009 | Jungkamp et al. | 558/308 |
| 7,541,486 B2 | 6/2009 | Scheidel et al. | |
| 7,700,795 B2 | 4/2010 | Haderlein et al. | |
| 2003/0023110 A1 * | 1/2003 | Tam et al. | 558/338 |
| 2003/0100802 A1 | 5/2003 | Shapiro | |
| 2003/0135014 A1 | 7/2003 | Radu et al. | |
| 2003/0212298 A1 | 11/2003 | Brasse et al. | |
| 2004/0063991 A1 | 4/2004 | Burattin et al. | |
| 2004/0106815 A1 | 6/2004 | Ritter | |
| 2004/0176622 A1 | 9/2004 | Bartsch et al. | |
| 2004/0235648 A1 | 11/2004 | Bartsch et al. | |
| 2004/0260112 A1 | 12/2004 | Basset et al. | |
| 2005/0090677 A1 | 4/2005 | Bartsch et al. | |
| 2005/0090678 A1 | 4/2005 | Bartsch et al. | |
| 2005/0247624 A1 | 11/2005 | Jungkamp et al. | |
| 2006/0142609 A1 | 6/2006 | Bourgeois et al. | |
| 2006/0175189 A1 | 8/2006 | Gerber et al. | |
| 2006/0252955 A1 | 11/2006 | Rosier et al. | |
| 2006/0258873 A1 | 11/2006 | Rosier et al. | |
| 2006/0258874 A1 | 11/2006 | Bartsch et al. | |
| 2006/0264651 A1 | 11/2006 | Bartsch et al. | |
| 2007/0060766 A1 | 3/2007 | Bartsch et al. | |
| 2007/0073071 A1 | 3/2007 | Haderlein et al. | |
| 2007/0083057 A1 | 4/2007 | Haderlein et al. | |
| 2007/0088173 A1 | 4/2007 | Haderlein et al. | |
| 2007/0112215 A1 | 5/2007 | Jungkamp et al. | |
| 2007/0155977 A1 | 7/2007 | Jungkamp et al. | |
| 2007/0155978 A1 | 7/2007 | Jungkamp et al. | |
| 2007/0155980 A1 | 7/2007 | Scheidel et al. | |
| 2007/0115936 A1 | 10/2007 | Haderlein et al. | |
| 2008/0015378 A1 | 1/2008 | Foo et al. | |
| 2008/0015380 A1 | 1/2008 | Foo et al. | |
| 2008/0015381 A1 | 1/2008 | Foo et al. | |
| 2008/0015382 A1 | 1/2008 | Foo et al. | |
| 2008/0071105 A1 | 3/2008 | Bartsch et al. | |
| 2008/0076944 A1 | 3/2008 | Bartsch et al. | |
| 2008/0083607 A1 | 4/2008 | Deckert et al. | |
| 2008/0221351 A1 | 9/2008 | Bartsch et al. | |
| 2008/0227214 A1 | 9/2008 | Jungkamp et al. | |
| 2008/0227998 A1 | 9/2008 | Scheidel et al. | |
| 2008/0242883 A1 | 10/2008 | Jungkamp et al. | |
| 2008/0242885 A1 | 10/2008 | Jungkamp et al. | |
| 2008/0242886 A1 * | 10/2008 | Bartsch et al. | 558/338 |
| 2008/0275266 A1 | 11/2008 | Bartsch et al. | |
| 2008/0281119 A1 | 11/2008 | Scheidel et al. | |
| 2008/0281120 A1 | 11/2008 | Jungkamp et al. | |
| 2009/0054671 A1 | 2/2009 | Haderlein et al. | |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1535179 A | 10/2004 |
| DE | 1807088 U | 3/1960 |
| DE | 1807088 A1 | 6/1969 |
| DE | 2055747 A1 | 5/1971 |
| DE | 1593277 B2 | 8/1973 |
| DE | 1593277 C3 | 3/1974 |
| DE | 2700904 C2 | 10/1983 |
| DE | 68909466 T2 | 3/1994 |
| DE | 10136488 A1 | 2/2003 |
| DE | 10150285 A1 | 4/2003 |
| DE | 10350999 A1 | 6/2005 |
| DE | 102004004696 A1 | 8/2005 |
| EP | 0001899 B1 | 3/1982 |
| EP | 123438 B1 | 7/1987 |
| EP | 160296 B1 | 10/1988 |
| EP | 268448 B1 | 9/1991 |

| | | | | | | |
|---|---|---|---|---|---|---|
| EP | 510689 | A1 | 10/1992 | EP | 1988998 A1 | 11/2008 |
| EP | 248643 | B1 | 3/1993 | EP | 1265832 B1 | 5/2009 |
| EP | 336314 | B1 | 9/1993 | EP | 1592659 B1 | 7/2009 |
| EP | 464691 | B1 | 12/1993 | EP | 1586598 B1 | 9/2009 |
| EP | 675871 | B1 | 4/1997 | EP | 2098106 A1 | 9/2009 |
| EP | 634395 | B1 | 9/1997 | EP | 1567478 B1 | 10/2009 |
| EP | 650959 | B1 | 9/1997 | EP | 1682559 B1 | 12/2009 |
| EP | 784610 | B1 | 2/1999 | EP | 1630166 B1 | 2/2010 |
| EP | 757672 | B1 | 6/1999 | FR | 1544656 A | 11/1968 |
| EP | 792259 | B1 | 8/1999 | FR | 2015115 A5 | 4/1970 |
| EP | 804412 | B1 | 12/1999 | FR | 1603513 A | 5/1971 |
| EP | 1000019 | A1 | 5/2000 | FR | 2069411 A5 | 9/1971 |
| EP | 1001928 | A1 | 5/2000 | FR | 2845379 B1 | 12/2004 |
| EP | 1003716 | A1 | 5/2000 | FR | 2873696 A1 | 2/2006 |
| EP | 1019190 | A1 | 7/2000 | FR | 2873696 B1 | 10/2006 |
| EP | 755302 | B1 | 10/2000 | GB | 0219474 A | 7/1924 |
| EP | 929513 | B1 | 4/2001 | GB | 1104140 A | 2/1968 |
| EP | 881924 | B1 | 5/2001 | GB | 1203702 A | 9/1970 |
| EP | 854858 | B1 | 6/2001 | GB | 1213175 A | 11/1970 |
| EP | 815073 | B1 | 7/2001 | GB | 1429169 A | 3/1976 |
| EP | 1144114 | A3 | 9/2001 | GB | 1429621 A | 3/1976 |
| EP | 1091804 | B1 | 2/2002 | GB | 1436932 A | 5/1976 |
| EP | 944585 | B1 | 4/2002 | GB | 1458322 A | 12/1976 |
| EP | 1000019 | B1 | 2/2003 | GB | 1482909 A | 8/1977 |
| EP | 911339 | B1 | 4/2003 | GB | 2007521 A | 5/1979 |
| EP | 1216268 | B1 | 11/2003 | GB | 1565443 A | 4/1980 |
| EP | 1350788 | A3 | 11/2003 | GB | 1594694 A | 8/1981 |
| EP | 1003607 | B1 | 12/2003 | GB | 2007521 B | 6/1982 |
| EP | 1003716 | B1 | 2/2004 | JP | 60044295 A | 3/1985 |
| EP | 1313743 | B1 | 3/2004 | JP | 1136333 U | 9/1989 |
| EP | 1414567 | A1 | 5/2004 | JP | 7188144 A | 7/1995 |
| EP | 1427695 | A1 | 6/2004 | MX | 2004PA002764 A | 6/2004 |
| EP | 1438133 | A1 | 7/2004 | WO | WO7900193 A1 | 4/1979 |
| EP | 1019190 | B1 | 12/2004 | WO | WO9414752 A1 | 7/1994 |
| EP | 1140801 | B1 | 2/2005 | WO | WO9514659 A1 | 6/1995 |
| EP | 1395547 | B1 | 3/2005 | WO | WO9528228 A1 | 10/1995 |
| EP | 1001928 | B1 | 4/2005 | WO | WO9529153 A1 | 11/1995 |
| EP | 1521736 | A1 | 4/2005 | WO | WO9611182 A1 | 4/1996 |
| EP | 1521737 | A1 | 4/2005 | WO | WO9616022 A1 | 5/1996 |
| EP | 1521738 | A2 | 4/2005 | WO | WO9622968 A1 | 8/1996 |
| EP | 1603865 | A1 | 12/2005 | WO | WO9629303 A1 | 9/1996 |
| EP | 1324976 | B1 | 2/2006 | WO | WO9703040 A1 | 1/1997 |
| EP | 1214975 | B1 | 3/2006 | WO | WO9712857 A1 | 4/1997 |
| EP | 1324978 | B1 | 3/2006 | WO | WO9724183 A1 | 7/1997 |
| EP | 1648860 | A1 | 4/2006 | WO | WO9736855 A2 | 10/1997 |
| EP | 891323 | B1 | 6/2006 | WO | WO9811051 A1 | 3/1998 |
| EP | 1226147 | B1 | 6/2006 | WO | WO9827054 A1 | 6/1998 |
| EP | 1438317 | B1 | 6/2006 | WO | WO9906146 A2 | 2/1999 |
| EP | 1682561 | A1 | 7/2006 | WO | WO9906356 | 2/1999 |
| EP | 1448668 | B1 | 8/2006 | WO | WO9906359 A1 | 2/1999 |
| EP | 1587621 | B1 | 8/2006 | WO | WO9913983 A1 | 3/1999 |
| EP | 1713759 | A1 | 10/2006 | WO | WO99/52632 | 10/1999 |
| EP | 1713761 | A1 | 10/2006 | WO | WO9964155 A1 | 12/1999 |
| EP | 1713762 | A1 | 10/2006 | WO | WO0001485 A2 | 1/2000 |
| EP | 1713766 | A1 | 10/2006 | WO | WO0037431 A1 | 6/2000 |
| EP | 1716102 | A2 | 11/2006 | WO | WO0121684 A1 | 3/2001 |
| EP | 1716103 | A1 | 11/2006 | WO | WO0136429 A1 | 5/2001 |
| EP | 1716104 | A1 | 11/2006 | WO | WO0168247 A2 | 9/2001 |
| EP | 1716105 | A1 | 11/2006 | WO | WO0211108 A1 | 2/2002 |
| EP | 1716106 | A1 | 11/2006 | WO | WO0213964 A2 | 2/2002 |
| EP | 1716107 | A1 | 11/2006 | WO | WO0218392 A1 | 3/2002 |
| EP | 1716109 | A2 | 11/2006 | WO | WO0226698 A1 | 4/2002 |
| EP | 1610893 | B1 | 3/2007 | WO | WO0230854 A2 | 4/2002 |
| EP | 1621531 | B1 | 3/2007 | WO | WO02053527 A1 | 7/2002 |
| EP | 1438132 | B1 | 4/2007 | WO | WO02092551 A2 | 11/2002 |
| EP | 1799697 | A1 | 6/2007 | WO | WO03011457 A1 | 2/2003 |
| EP | 1713764 | B1 | 8/2007 | WO | WO03018540 A1 | 3/2003 |
| EP | 1713816 | B1 | 8/2007 | WO | WO03024919 A1 | 3/2003 |
| EP | 1825914 | A1 | 8/2007 | WO | WO03031392 A1 | 4/2003 |
| EP | 1448620 | B1 | 6/2008 | WO | WO03033141 A1 | 4/2003 |
| EP | 1817108 | B1 | 6/2008 | WO | WO03033509 A1 | 4/2003 |
| EP | 1713760 | B1 | 7/2008 | WO | WO03046019 A1 | 6/2003 |
| EP | 1571172 | B1 | 10/2008 | WO | WO03046049 A1 | 6/2003 |

| | | | |
|---|---|---|---|
| WO | WO03068729 A1 | 8/2003 |
| WO | WO03076394 A1 | 9/2003 |
| WO | WO2004007431 A1 | 1/2004 |
| WO | WO2004007432 A1 | 1/2004 |
| WO | WO2004007435 A2 | 1/2004 |
| WO | WO2004007508 A2 | 1/2004 |
| WO | WO0168247 | 6/2004 |
| WO | WO2004060855 A1 | 7/2004 |
| WO | WO2004064994 A2 | 8/2004 |
| WO | WO2004065352 A2 | 8/2004 |
| WO | WO2004080924 A2 | 9/2004 |
| WO | WO2004080948 A1 | 9/2004 |
| WO | WO2004087314 A1 | 10/2004 |
| WO | WO2005019160 A1 | 3/2005 |
| WO | WO2005/042547 | 5/2005 |
| WO | WO2005042156 A1 | 5/2005 |
| WO | WO2005042157 A2 | 5/2005 |
| WO | WO2005042547 A1 | 5/2005 |
| WO | WO2005042549 A1 | 5/2005 |
| WO | WO 2005/073170 * | 8/2005 |
| WO | WO 2005/073173 * | 8/2005 |
| WO | WO2005073167 A1 | 8/2005 |
| WO | WO2005073168 A1 | 8/2005 |
| WO | WO2005073169 A1 | 8/2005 |
| WO | WO2005073170 A1 | 8/2005 |
| WO | WO2005073171 A1 | 8/2005 |
| WO | WO2005073172 A1 | 8/2005 |
| WO | WO2005073173 A1 | 8/2005 |
| WO | WO2005073174 A1 | 8/2005 |
| WO | WO2005073175 A1 | 8/2005 |
| WO | WO2005073176 A1 | 8/2005 |
| WO | WO2005073178 A2 | 8/2005 |
| WO | WO2005073179 A1 | 8/2005 |
| WO | WO2005073241 A1 | 8/2005 |
| WO | WO2006040023 A1 | 4/2006 |
| WO | WO2006042675 A2 | 4/2006 |
| WO | WO2005073166 A3 | 3/2007 |
| WO | WO2007051374 A1 | 5/2007 |
| WO | WO2007096274 A1 | 8/2007 |
| WO | WO2007115936 A2 | 10/2007 |
| WO | WO2008008926 A2 | 1/2008 |
| WO | WO2008008928 A2 | 1/2008 |
| WO | WO2008008929 A2 | 1/2008 |
| WO | WO2008008930 A2 | 1/2008 |
| WO | WO2008028843 A1 | 3/2008 |
| WO | WO2008062058 A1 | 5/2008 |

* cited by examiner

PROCESS FOR MAKING 3-PENTENENITRILE BY HYDROCYANATION OF BUTADIENE

CROSS-REFERENCE TO RELATED APPLICATIONS

This application claims benefit of priority from Provisional Application No. 60/830,970, filed Jul. 14, 2006. This application hereby incorporates by reference Provisional Application No. 60/830,970 in its entirety. This application relates to commonly-assigned applications filed concurrently on Jul. 12, 2007.

FIELD OF THE INVENTION

The invention relates to the hydrocyanation of 1,3-butadiene to produce 3-pentenenitriles and other unsaturated nitrites. More particularly, this invention relates to a process for the hydrocyanation of 1,3-butadiene using a catalyst precursor composition comprising a zero-valent nickel and at least one multidentate phosphorus-containing ligand.

BACKGROUND OF THE INVENTION

3-Pentenenitrile (3PN) is an important intermediate in the production of adiponitrile (ADN). ADN is of particular interest because it is a commercially versatile and important intermediate in the industrial production of nylon polyamides useful in forming films, fibers, and molded articles.

It is well known in the art that 3PN may be formed through a series of reactions as illustrated in Equations 1 and 2 below,

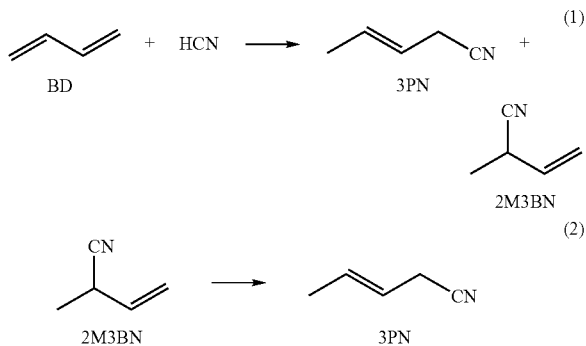

wherein BD is butadiene, HCN is hydrogen cyanide, and 2M3BN is the BD hydrocyanation co-product 2-methyl-3-butenenitrile. U.S. Pat. No. 3,496,215 describes the catalytic hydrocyanation of BD (equation 1) in the presence of $NiL_4$ complexes wherein L is a monodentate phosphorus containing ligand. The relative amounts of 3PN and 2M3BN can be dependent upon the catalyst utilized in this chemical reaction. U.S. Pat. No. 3,536,748 describes the catalytic isomerization of 2M3BN to 3PN (equation 2) in the presence of $NiL_4$ complexes.

U.S. Pat. No. 3,536,748 discloses that in the presence of HCN, the nickel complex preferentially catalyzes formation of undesired, six-carbon, saturated dinitrile (2-methylglutaronitrile, MGN) from 2M3BN (see equation 3 below). This patent notes that, because of the overriding competitive hydrocyanation reaction, for the isomerization of 2M3BN to 3PN it is necessary to avoid the presence of large amounts of HCN, for example any amount of the order of or in excess of 1:1 mole ratio with the 2M3BN starting material. The reference further discloses that HCN has no significant effect per se on the isomerization reaction, its presence in minor amounts in the starting material can be tolerated if necessary, and the isomerization process is preferably conducted in the absence of HCN.

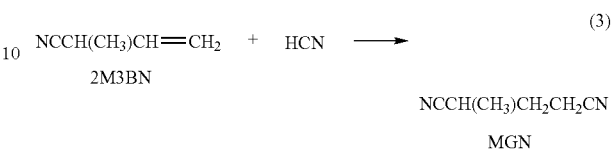

U.S. Pat. No. 6,169,198 discloses that hydrocyanation of BD to prepare ADN can generally be divided into three steps. The first is synthesis of mononitriles by hydrocyanation of BD (as in Equation 1 above), for which the selectivity for the linear 3PN is about 70% or less, depending on the catalyst used. The second is isomerization of the 2M3BN present in the mixtures to 3PN (as in Equation 2 above) and isomerization of 3PN to various n-pentenenitriles; the third is synthesis of dinitriles. Also disclosed is a preferred embodiment in which the ratio of the amounts of 3PN to 2M3BN obtained in the monoaddition of HCN onto the BD-containing hydrocarbon mixture is at least 5:1, preferably at least 10:1, in particular at least 20:1, with a catalyst comprising at least one metallocene-phosphorus(III)-nickel(0) complex. The reference further discloses that it is generally possible to dispense with division of the process for preparing ADN into the three steps of monoaddition of HCN onto a BD-containing hydrocarbon mixture; isomerization; addition of HCN onto 4-pentenenitrile (4PN) formed in situ; and the addition of 2 mole equivalents of HCN onto a BD-containing hydrocarbon mixture can be designed as a one-stage process.

In recent years, a new class of catalysts has been described for the transformations of Equations 1 and 2. U.S. Pat. Nos. 5,512,695; 5,512,696; 5,523,453; 5,663,369; 5,688,986; 5,693,843; 5,723,641; 5,821,378; 5,959,135; 5,981,772; 6,020,516; 6,127,567; 6,171,996; 6,171,997; and WO99/52632 describe the use of diphosphite and diphosphinite nickel complexes as catalysts for the hydrocyanation of BD or 3PN and the isomerization of 2M3BN to 3PN. In general, this class of catalysts is characterized by greater catalytic activity and resistance to HCN-derived degradation reactions compared to the catalysts comprising nickel complexes of monodentate phosphites and phosphinites. As a result, this new class of catalysts may generally be used effectively at much lower concentrations and over a broader range of reaction conditions. U.S. Pat. Nos. 5,821,378; 5,981,772 and 6,020,516 describe the capability of a limited number of these catalyst systems to isomerize 2M3BN at the same temperature at which BD is hydrocyanated.

It would be desirable to have a high yield 3PN process in which BD hydrocyanation and 2M3BN isomerization occur concurrently in the same reaction zone. Such a combined BD hydrocyanation/2M3BN isomerization process would have fewer reaction and process separation steps than a process in which the hydrocyanation and isomerization reactions were performed, for example, in separate reaction zones under reaction conditions optimized independently for BD hydrocyanation or for 2M3BN isomerization to 3PN. The advantages of a combined BD hydrocyanation/2M3BN isomerization process having simplified process complexity could include reduced capital investment and reduced cost of manufacture. Reduced yield loss to undesired by-products, such as MGN and compounds derived from BD dimerization and/or oligomerization, might also be realized with a combined BD hydrocyanation/2M3BN isomerization process.

SUMMARY OF THE INVENTION

In a first aspect, the present invention can provide a process for the continuous production of 3-pentenenitrile, comprising: (a) contacting, in a reaction zone, a hydrogen cyanide (HCN)-containing feed, a butadiene (BD)-containing feed, and a catalyst precursor composition, wherein the catalyst precursor composition comprises a zero-valent nickel and at least one multidentate phosphorus-containing ligand selected from the group consisting of a phosphite, a phosphonite, a phosphinite, a phosphine, and a mixed phosphorus-containing ligand or a combination of such members; and (b) maintaining a residence time in the reaction zone sufficient to convert about 95% or more of the hydrogen cyanide and to produce a reaction mixture comprising 3-pentenenitrile and 2-methyl-3-butenenitrile, wherein the 2-methyl-3-butenenitrile concentration is maintained below about 15 weight percent of the total mass of the reaction mixture.

Another aspect of the present invention is the process wherein the molar ratio of the hydrogen cyanide in the feed to the butadiene in the feed is in the range of about 0.90:1.00 to about 1.04:1.00, and the molar ratio of the zero-valent nickel in the feed to the butadiene in the feed is in the range of about 0.00005:1.00 to about 0.0050:1.00.

Another aspect of the present invention is the process wherein the temperature is maintained within a range of about 80° C. to about 140° C.

Another aspect of the present invention is the process wherein the temperature is maintained within the range of about 100° C. to about 130° C.

Another aspect of the present invention is the process wherein the multidentate phosphorus-containing ligand is a phosphite.

Another aspect of the present invention is the process wherein the multidentate phosphorus-containing ligand is a phosphonite.

Another aspect of the present invention is the process wherein the multidentate phosphorus-containing ligand is a phosphinite.

Another aspect of the present invention is the process wherein the multidentate phosphorus-containing ligand is a phosphine.

Another aspect of the present invention is the process wherein the multidentate phosphorus-containing ligand is a mixed phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

Another aspect of the present invention is the process wherein the molar ratio of the hydrogen cyanide in the feed to the butadiene in the feed is in the range of about 0.92:1.00 to about 0.98:1.00.

Another aspect of the present invention is the process wherein the molar ratio of the zero-valent nickel in the feed to the butadiene in the feed is in the range of about 0.0001:1.00 to about 0.0010:1.00.

Another aspect of the present invention is the process wherein the residence time is sufficient to maintain the 2-methyl-3-butenenitrile concentration at or below about 10 wt % of the total mass of the reaction mixture.

Another aspect of the present invention is the process further comprising optionally contacting a feed comprising 2-methyl-3-butenenitrile in the reactor.

Another aspect of the present invention is the process wherein the catalyst precursor composition further comprises at least one monodentate phosphorus-containing ligand selected from the group consisting of a phosphite, a phosphonite, a phosphinite, and a phosphine or a combination of such members.

Another aspect of the present invention is the process wherein the multidentate phosphorus-containing ligand is a bidentate phosphite.

Another aspect of the present invention is the process wherein the multidentate phosphorus-containing ligand is a bidentate phosphonite.

Another aspect of the present invention is the process wherein the multidentate phosphorus-containing ligand is a bidentate phosphinite.

Another aspect of the present invention is the process wherein the multidentate phosphorus-containing ligand is a bidentate phosphine.

Another aspect of the present invention is the process wherein the multidentate phosphorus-containing ligand is a bidentate mixed phosphorus-containing ligand selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

DETAILED DESCRIPTION OF THE INVENTION

The invention provides a process for the continuous production of 3-pentenenitrile in which a HCN-containing feed, a BD-containing feed, and a catalyst precursor composition solution are contacted, for example concurrently, in a reaction zone, for example a continuous-stirred-tank-reactor (CSTR), and a residence time is maintained sufficient to convert about 95% or more of the HCN and to produce a reaction mixture comprising 3PN and 2M3BN, wherein the 2M3BN concentration is maintained below about 15 weight percent of the total mass of the reaction mixture.

In another aspect, the process of the invention further comprises optionally contacting a feed comprising 2M3BN in the reaction zone. The 2M3BN in the feed can be produced by a different process or prepared in a separate manufacturing facility. Alternatively, the 2M3BN in the feed may be obtained from a BD hydrocyanation and/or 2M3BN isomerization process as described in the art or the process of the current invention wherein a stream comprising 2M3BN may be, for example, distilled from a higher boiling reaction product comprising 3PN. Such a stream comprising 2M3BN can be recycled to the reaction zone of the present invention in which BD hydrocyanation and 2M3BN isomerization occurs. Potential advantages of such a process can include the elimination of investment and of the associated variable and fixed costs for operating an additional 2M3BN isomerization reaction vessel, distillation columns, and the associated pumps, heat exchangers, piping, and control instrumentation.

In processes falling within the scope of the present invention, the hydrocyanation and isomerization reactions of Equations 1 and 2 (above) can be carried out concurrently and continuously in the same reaction zone, for example under high BD and HCN conversion conditions.

The catalyst precursor composition comprises a zero-valent nickel and at least one multidentate phosphorus-containing (P-containing) ligand selected from the group consisting of a phosphite, a phosphonite, a phosphinite, a phosphine, and a mixed P-containing ligand or a combination of such members. As used herein, the term "mixed P-containing ligand" means a multidentate phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

The catalyst precursor compositions may further comprise at least one monodentate P-containing ligand selected from the group consisting of a phosphite, a phosphonite, a phosphinite, and a phosphine or a combination of such members, provided that the monodentate P-containing ligand does not detract from the beneficial aspects of the invention. The monodentate P-containing ligand may be present as an impurity from the synthesis of the multidentate P-containing ligand, or the monodentate P-containing ligand may be added as an additional component of the catalyst precursor composition.

Each catalyst precursor composition useful in the present invention may be considered a "precursor" composition in that the zero-valent nickel at some point becomes bound to at least one multidentate P-containing ligand, and further in all likelihood, additional reactions occur during hydrocyanation, such as, for example, complexing of the initial catalyst composition to an ethylenically unsaturated compound.

As used herein, the term "catalyst precursor composition" also includes within its meaning recycled catalyst, that is, a catalyst precursor composition comprising a zero-valent nickel and at least one multidentate P-containing ligand which, having been used in the process of the invention, is returned or may be returned to the process and used again.

The term "hydrocarbyl" is well known in the art and designates a hydrocarbon molecule from which at least one hydrogen atom has been removed. Such molecules can contain single, double, or triple bonds.

The term "aryl" is well-known in the art and designates an aromatic hydrocarbon molecule from which at least one hydrogen atom has been removed.

Examples of suitable aryl groups include those containing 6 to 10 carbon atoms, which can be unsubstituted or singly or multiply substituted. Suitable substituents include, for example, $C_1$-$C_4$ hydrocarbyl, or halogen such as fluorine, chlorine or bromine, or halogenated hydrocarbyl such a trifluoromethyl, or aryl such as phenyl.

The P-containing ligand may be multidentate, for example bidentate, or tridentate. The P-containing ligand may be selected from the group consisting of a phosphite, a phosphonite, a phosphinite, a phosphine, and a mixed P-containing ligand or a combination of such members. The multidentate P-containing ligand may be represented by Formula I

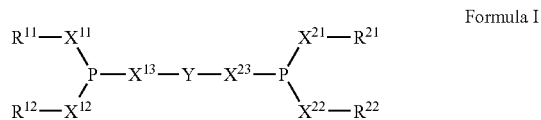

Formula I wherein $X^{11}, X^{12}, X^{13}, X^{21}, X^{22}, X^{23}$ independently represent oxygen or a single bond, $R^{11}, R^{12}$ independently represent identical or different, single or bridged organic radicals, $R^{21}, R^{22}$ independently represent identical or different, single or bridged organic radicals, and Y represents a bridging group.

It is to be understood that Formula I may represent a single compound or a mixture of different compounds having the indicated structure.

In one embodiment, all of the groups $X^{11}, X^{12}, X^{13}, X^{21}, X^{22}, X^{23}$ may represent oxygen. In such a case, the bridging group Y is joined to phosphite groups. In such a case, the multidentate P-containing ligand represented by Formula I is a phosphite.

In another embodiment, $X^{11}$ and $X^{12}$ may each represent oxygen, and $X^{13}$, a single bond; or $X^{11}$ and $X^{13}$ may each represent oxygen and $X^{12}$, a single bond, so that the phosphorus atom surrounded by $X^{11}, X^{12}$, and $X^{13}$ is the central atom of a phosphonite. In such a case, $X^{21}, X^{22}$, and $X^{23}$ may each represent oxygen, so that the phosphorus atom surrounded by $X^{21}, X^{22}$, and $X^{23}$ may be the central atom of a phosphite; or $X^{21}$ and $X^{22}$ may each represent oxygen and $X^{23}$, a single bond; or $X^{21}$ and $X^{23}$ may each represent oxygen and $X^{22}$, a single bond, so that the phosphorus atom surrounded by $X^{21}, X^{22}$, and $X^{23}$ may be the central atom of a phosphonite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}, X^{22}$, and $X^{23}$ may be the central atom of a phosphinite; or $X^{21}, X^{22}$, and $X^{23}$ may each represent a single bond, so that the phosphorus atom surrounded by $X^{21}, X^{22}$, and $X^{23}$ may be the central atom of a phosphine.

When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphite, the multidentate ligand represented by Formula I is a phosphite-phosphonite and is an example of a mixed P-containing ligand. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphonite, the multidentate P-containing ligand represented by Formula I is a phosphonite. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphinite, the multidentate P-containing ligand represented by Formula I is a phosphonite-phosphinite and is an example of a mixed P-containing ligand. When the phosphorus atom surrounded by $X^{11}, X^{12}$, and $X^{13}$ is the central atom of a phosphonite and the phosphorus atom surrounded by $X^{21}, X^{22}$, and $X^{23}$ is the central atom of a phosphine, the multidentate P-containing ligand represented by Formula I is a phosphonite-phosphine and is an example of a mixed P-containing ligand.

In another embodiment, $X^{13}$ may represent oxygen and $X^{11}$ and $X^{12}$, each a single bond; or $X^{11}$ may represent oxygen and $X^{12}$ and $X^{13}$, each a single bond, so that the phosphorus atom surrounded by $X^{11}, X^{12}$, and $X^{13}$ is the central atom of a phosphinite. In such a case, $X^{21}, X^{22}$, and $X^{23}$ may each represent oxygen, so that the phosphorus atom surrounded by $X^{21}, X^{22}$, and $X^{23}$ may be the central atom of a phosphite; or $X^{23}$ may represent oxygen and $X^{21}$ and $X^{22}$, each a single bond; or $X^{21}$ may represent oxygen and $X^{22}$ and $X^{23}$, each a single bond, so that the phosphorus atom surrounded by $X^{21}, X^{22}$, and $X^{23}$ may be the central atom of a phosphinite; or $X^{21}, X^{22}$, and $X^{23}$ may each represent a single bond, so that the phosphorus atom surrounded by $X^{21}, X^{22}$, and $X^{23}$ may be the central atom of a phosphine.

When the phosphorus atom surrounded by $X^{11}, X^{12}$, and $X^{13}$ is the central atom of a phosphinite and the phosphorus atom surrounded by $X^{21}, X^{22}$, and $X^{23}$ is the central atom of a phosphite, the multidentate P-containing ligand represented by Formula I is a phosphite-phosphinite and is an example of a mixed P-containing ligand. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphinite, the multidentate P-containing ligand represented by Formula I is a phosphinite. When the phosphorus atom surrounded by $X^{11}$, $X^{12}$, and $X^{13}$ is the central atom of a phosphinite and the phosphorus atom surrounded by $X^{21}$, $X^{22}$, and $X^{23}$ is the central atom of a phosphine, the multidentate P-containing ligand represented by Formula I is a phosphinite-phosphine and is an example of a mixed P-containing ligand.

In another embodiment, $X^{11}$, $X^{12}$, and $X^{13}$ may each represent a single bond, so that the phosphorus atom surrounded by $X^{11}$, $X^{12}$, and $X^{13}$ is the central atom of a phosphine. In such a case, $X^{21}$, $X^{22}$, and $X^{23}$ may each represent oxygen, so that the phosphorus atom surrounded by $X^{21}$, $X^{22}$, and $X^{23}$ may be the central atom of a phosphite; or $X^{21}$, $X^{22}$, and $X^{23}$ may each represent a single bond, so that the phosphorus atom surrounded by $X^{21}$, $X^{22}$, and $X^{23}$ may be the central atom of a phosphine.

When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphite, the multidentate P-containing ligand represented by Formula I is a phosphite-phosphine and is an example of a mixed P-containing ligand. When the phosphorus atom surrounded by $X^{11}$, $X^{12}$, and $X^{13}$ is the central atom of a phosphine and the phosphorus atom surrounded by $X^{21}$, $X^{22}$, and $X^{23}$ is the central atom of a phosphine, the multidentate P-containing ligand represented by Formula I is a phosphine.

Bridging group Y may be aryl groups substituted, for example, with $C_1$-$C_4$ hydrocarbyl, or halogen such as fluorine, chlorine, or bromine, or halogenated hydrocarbyl such as trifluoromethyl, or aryl such as phenyl, or unsubstituted aryl groups, for example those with 6 to 20 carbon atoms in the aromatic system, for example 2,2'-biphenyl and 1,1'-bi-2-naphthyl.

Radicals $R^{11}$ and $R^{12}$ may independently represent identical or different organic radicals. $R^{11}$ and $R^{12}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{21}$ and $R^{22}$ may independently represent identical or different organic radicals. $R^{21}$ and $R^{22}$ may be aryl radicals, for example those containing 6 to 10 carbon atoms, which can be unsubstituted or singly or multiply substituted, for example by $C_1$-$C_4$ hydrocarbyl, or halogen such as fluorine, chlorine, or bromine, or halogenated hydrocarbyl such as trifluoromethyl, or aryl such as phenyl, or unsubstituted aryl groups.

Radicals $R^{11}$ and $R^{12}$ may be single or bridged. Radicals $R^{21}$ and $R^{22}$ may also be single or bridged. Radicals $R^{11}$, $R^{12}$, $R^{21}$, and $R^{22}$ may all be single, or two may be bridged and two single, or all four may be bridged in the manner described.

Examples of multidentate P-containing ligands include the following:
1) the compounds of Formula I, II, III, IV, and V disclosed in U.S. Pat. No. 5,723,641;
2) the compounds of Formula I, II, III, IV, V, VI, and VII disclosed in U.S. Pat. No. 5,512,696, for example the compounds used in Examples 1 through 31 therein;
3) the compounds of Formula I, II, III, IV, V, VI, VII, VIII, IX, X, XI, XII, XIII, XIV, and XV disclosed in U.S. Pat. No. 5,821,378, for example the compounds used in Examples 1 through 73 therein;
4) the compounds of Formula I, II, III, IV, V, and VI disclosed in U.S. Pat. No. 5,512,695, for example the compounds used in Examples 1 through 6 therein;
5) the compounds of Formula I, II, III, IV, V, VI, VII, VIII, IX, X, XI, XII, XIII, and XIV disclosed in U.S. Pat. No. 5,981,772, for example the compounds used in Examples 1 through 66 therein;
6) the compounds disclosed in U.S. Pat. No. 6,127,567, for example the compounds used in Examples 1 through 29 therein;
7) the compounds of Formula I, II, III, IV, V, VI, VII, VIII, IX, and X disclosed in U.S. Pat. No. 6,020,516, for example the compounds used in Examples 1 through 33 therein;
8) the compounds disclosed in U.S. Pat. No. 5,959,135, for example the compounds used in Examples 1 through 13 therein;
9) the compounds of Formula I, II, and III disclosed in U.S. Pat. No. 5,847,191;
10) the compounds disclosed in U.S. Pat. No. 5,523,453, for example the compounds of Formula 1, 2, 3, 4, 5, 6, 7, 8, 9, 10, 11, 12, 13, 14, 15, 16, 17, 18, 19, 20, and 21 therein;
11) the compounds disclosed in U.S. Pat. No. 5,693,843, for example the compounds of Formula I, II, III, IV, V, VI, VII, VIII, IX, X, XI, XII, and XIII, for example the compounds used in Examples 1 through 20 therein;
12) the compounds of Formula V, VI, VII, VIII, IX, X, XI, XII, XIII, XIV, XV, XVI, XVII, XVIII, XIX, XX, XXI, XXII, XXIII, XXIV, XXV, and XXVI disclosed in U.S. Pat. No. 6,893,996;
13) the compounds disclosed in published patent application WO 01/14392, for example the compounds illustrated in Formula V, VI, VII, VIII, IX, X, XI, XII, XIII, XIV, XV, XVI, XVII, XXI, XXII, and XXIII therein;
14) the chelating compounds disclosed in U.S. Pat. No. 6,242,633, for example the compounds of Formula If, Ig, and Ih;
15) the compounds disclosed in U.S. Pat. No. 6,521,778, for example the compounds of Formula I, Ia, Ib, and Ic, for example the compounds referred to as Ligand I and II;
16) the compounds disclosed in published patent application WO 02/13964, for example the compounds of Formula Ia, Ib, Ic, Id, Ie, If, Ig, Ih, Ii, Ij, and Ik, for example the compounds referred to as Ligand 1, 2, 3, 4, 5, and 6;
17) the compounds disclosed in German Patent Application DE 100 460 25;
18) the chelating compounds disclosed in U.S. Pat. No. 7,022,866, for example the compounds of Formula 1 and 2, for example the compounds referred to as Ligand 1 and 2;
19) the compounds disclosed in United States Published Patent Application No. 2005/0090677, for example the compounds of Formula 1, 1a, 1b, 1c, 1d, 1e, 1f, 1g, 1h, 1i, 1j, 1k, 1l, 1m, 1n, 1o, 2, and 3;
20) the compounds disclosed in United States Published Patent Application No. 2005/0090678, for example the compounds of Formula 1 and 2, for example the compounds referred to as Ligand 1, 2, 3, 4, 5, and 6;
21) the compounds disclosed in published patent application WO 2005/042547, for example the compounds of Formula 1, 1a, 1b, 1c, 1d, 1e, 1f, 1g, 1h, 1i, 1j, 1k, 1l, 1m, 1n, 1o, 2, 3, 4, 5, and 6, for example the compounds referred to as Ligand 1, 2, 3, and 4;

22) the chelating compounds disclosed in U.S. Pat. No. 6,169,198, for example the compounds of Formula I; and 23) the compounds disclosed in U.S. Pat. No. 6,660,877, for example the compounds of Formula I, II, and III, for example the compounds used in Examples 1 through 25 therein.

These references also disclose methods for preparing multidentate ligands of Formula I.

Further examples of the multidentate P-containing ligand include a bidentate phosphite ligand selected from a member of the group represented by Formulas II and III, in which all like reference characters have the same meaning, except as further explicitly limited:

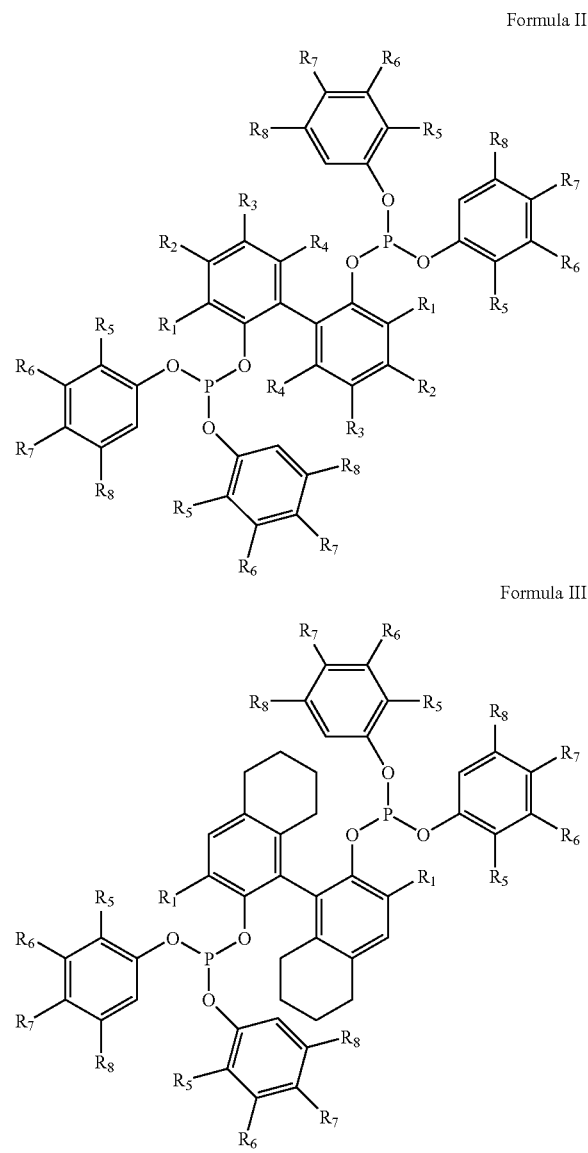

Formula II

Formula III wherein $R_1$ and $R_5$ are independently selected from the group consisting of $C_1$ to $C_5$ hydrocarbyl, and $R_2$, $R_3$, $R_4$, $R_6$, $R_7$ and $R_8$ are independently selected from the group consisting of H and $C_1$ to $C_4$ hydrocarbyl.

It will be recognized that Formula II and Formula III are two dimensional representations of three-dimensional molecules and that rotation about chemical bonds can occur in the molecules to give configurations differing from those shown. For example, rotation about the carbon-carbon bond between the 2- and 2'-positions of the biphenyl and octahydrobinaphthyl bridging groups of Formula II and Formula III, respectively, can bring the two phosphorus atoms of each Formula in closer proximity to one another and can allow the phosphite ligand to bind to a single nickel atom in a bidentate fashion. The term "bidentate" is well known in the art and means both phosphorus atoms of the ligand are bonded to a single nickel atom.

For example, the multidentate P-containing ligand can be selected from a member of the group represented by Formulas II and III, wherein
  $R_1$ is methyl, ethyl, isopropyl or cyclopentyl;
  $R_2$ is H or methyl;
  $R_3$ is H or a $C_1$ to $C_4$ hydrocarbyl;
  $R_4$ is H or methyl;
  $R_5$ is methyl, ethyl or isopropyl; and
  $R_6$, $R_7$ and $R_8$ are independently selected from the group consisting of H and $C_1$ to $C_4$ hydrocarbyl.

As additional examples, the multidentate P-containing ligand can be selected from a member of the group represented by Formula II, wherein
  $R_1$, $R_4$, and $R_5$ are methyl;
  $R_2$, $R_6$, $R_7$ and $R_8$ are H; and
  $R_3$ is a $C_1$ to $C_4$ hydrocarbyl;
or
  $R_1$ is isopropyl;
  $R_2$ is H;
  $R_3$ is a $C_1$ to $C_4$ hydrocarbyl;
  $R_4$ is H or methyl;
  $R_5$ is methyl or ethyl;
  $R_6$ and $R_8$ are H or methyl; and
  $R_7$ is H, methyl or tertiary-butyl;

or the multidentate P-containing ligand can be selected from a member of the group represented by Formula III, wherein
  $R_1$ is isopropyl or cyclopentyl;
  $R_5$ is methyl or isopropyl; and
  $R_6$, $R_7$, and $R_8$ are H.

As yet another example, the multidentate P-containing ligand can be represented by Formula II, wherein $R_1$ is isopropyl; $R_2$, $R_6$, and $R_8$ are H; and $R_3$, $R_4$, $R_5$, and $R_7$ are methyl.

The multidentate P-containing ligand may also be a polymeric ligand composition, as disclosed, for example, in U.S. Pat. Nos. 6,284,865; 6,924,345, or United States Published Patent Application No. 2003/135014. Methods for preparing such polymeric ligand compositions are well known in the art and are disclosed, for example, in the above cited references.

The catalyst precursor compositions may further comprise at least one monodentate P-containing ligand selected from the group consisting of a phosphite, a phosphonite, a phosphinite, and a phosphine or a combination of such members. The monodentate P-containing ligand may be added as an additional component of the catalyst precursor composition, or it may be present, for example, as an impurity from the synthesis of the multidentate P-containing ligand. The monodentate P-containing ligand may be represented by Formula IV $$P(X^1R^{31})(X^2R^{32})(X^3R^{33})$$  Formula IV wherein
  $X^1$, $X^2$, $X^3$ independently represent oxygen or a single bond, and $R^{31}$, $R^{32}$, $R^{33}$ independently represent identical or different, single or bridged organic radicals.

It is to be understood that Formula IV may be a single compound or a mixture of different compounds having the indicated structure.

In one embodiment, all of the groups $X^1$, $X^2$, and $X^3$ may represent oxygen, so that Formula IV represents a phosphite of formula $P(OR^{31})(OR^{32})(OR^{33})$, wherein $R^{31}$, $R^{32}$, and $R^{33}$ have the meanings defined herein.

If one of the groups $X^1$, $X^2$, and $X^3$ represents a single bond and two groups represent oxygen, Formula IV represents a phosphonite of formula $P(OR^{31})(OR^{32})(R^{33})$, $P(R^{31})(OR^{32})(OR^{33})$, or $P(OR^{31})(R^{32})(OR^{33})$, wherein $R^{31}$, $R^{32}$, and $R^{33}$ have the meanings defined herein.

If two of the groups $X^1$, $X^2$, and $X^3$ represent single bonds and one group represents oxygen, Formula IV represents a phosphinite of formula $P(OR^{31})(R^{32})(R^{33})$ or $P(R^{31})(OR^{32})(R^{33})$ or $P(R^{31})(R^{32})(OR^{33})$, wherein $R^{31}$, $R^{32}$, and $R^{33}$ have the meanings defined herein.

The groups $X^1$, $X^2$, $X^3$ may independently represent oxygen or a single bond. If all the groups $X^1$, $X^2$, and $X^3$ represent single bonds, Formula IV represents a phosphine of formula $P(R^{31})(R^{32})(R^{33})$, wherein $R^{31}$, $R^{32}$, and $R^{33}$ have the meanings defined herein.

Radicals $R^{31}$, $R^{32}$, and $R^{33}$ may independently represent identical or different organic radicals, for example hydrocarbyl radicals comprising 1 to 10 carbon atoms, such as methyl, ethyl, n-propyl, isopropyl, n-butyl, isobutyl, s-butyl, and t-butyl, aryl groups such as phenyl, o-tolyl, m-tolyl, p-tolyl, 1-naphthyl, or 2-naphthyl, or hydrocarbyl radicals comprising 1 to 20 carbon atoms, such as 1,1'-biphenol or 1,1'-binaphthol. The $R^{31}$, $R^{32}$, and $R^{33}$ radicals may be connected to one another directly, meaning not solely via the central phosphorus atom. Alternatively, the $R^{31}$, $R^{32}$, and $R^{33}$ radicals may be not directly connected to one another.

For example, $R^{31}$, $R^{32}$, and $R^{33}$ may be selected from the group composed of phenyl, o-tolyl, m-tolyl, and p-tolyl. As another example, a maximum of two of the $R^{31}$, $R^{32}$, and $R^{33}$ groups may be phenyl. Alternatively, a maximum of two of the $R^{31}$, $R^{32}$, and $R^{33}$ groups may be o-tolyl.

Compounds of Formula IVa,

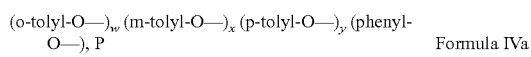  Formula IVa may be used as the monodentate P-containing ligand, wherein w, x, y, and z are integers, and the following conditions apply: w+x+y+z=3 and w, z≦2.

Examples of compounds of Formula IVa include (p-tolyl-O—)(phenyl-O—)$_2$P, (m-tolyl-O—)(phenyl-O—)$_2$P, (o-tolyl-O—)(phenyl-O—)$_2$P, (p-tolyi-O—)2(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O—)(phenyl-O—) P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P, (o-tolyl-O—)$_2$(m-tolyl-O—)P, or mixtures of such compounds.

Mixtures containing (m-tolyl-O—)$_3$P, (m-tolyl-O—)$_2$(p-tolyl-O—)P, (m-tolyl-O—)(p-tolyl-O—)$_2$P, and (p-tolyl-O—)$_3$P may be obtained, for example, by reacting a mixture containing m-cresol and pcresol, in particular in a molar ratio of 2:1 as occurs in the distillative processing of crude oil, with a phosphorus trihalide such as phosphorus trichloride.

Additional examples of monodentate P-containing ligands are the phosphites disclosed in U.S. Pat. No. 6,770,770 and referred to herein as phosphites of Formula IVb,

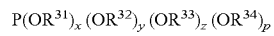  Formula IVb wherein $R^{31}$ is an aromatic radical having a $C_1$-$C_{18}$ alkyl substituent in the o-position relative to the oxygen atom which connects the phosphorus atom to the aromatic system, or having an aromatic substituent in the o-position relative to the oxygen atom which connects the phosphorus atom to the aromatic system, or having an aromatic system fused on in the o-position relative to the oxygen atom which connects the phosphorus atom to the aromatic system;

$R^{32}$ is an aromatic radical having a $C_1$-$C_{18}$ alkyl substituent in the m-position relative to the oxygen atom which connects the phosphorus atom to the aromatic system, or having an aromatic substituent in the m-position relative to the oxygen atom which connects the phosphorus atom to the aromatic system, or having an aromatic system fused on in the m-position relative to the oxygen atom which connects the phosphorus atom to the aromatic system, where the aromatic radical bears a hydrogen atom in the o-position relative to the oxygen atom which connects the phosphorus atom to the aromatic system;

$R^{33}$ is an aromatic radical having a $C_1$-$C_{18}$ alkyl substituent in the p-position relative to the oxygen atom which connects the phosphorus atom to the aromatic system, or having an aromatic substituent in the p-position relative to the oxygen atom which connects the phosphorus atom to the aromatic system, where the aromatic radical bears a hydrogen atom in the o-position relative to the oxygen atom which connects the phosphorus atom to the aromatic system;

$R^{34}$ is an aromatic radical which bears substituents other than those defined for $R^{31}$, $R^{32}$, and $R^{33}$ in the o-, m-, and p-position relative to the oxygen atom which connects the phosphorus atom to the aromatic system, where the aromatic radical bears a hydrogen atom in the o-position relative to the oxygen atom which connects the phosphorus atom to the aromatic system;

x is 1 or 2; and y, z, and p independently of one another is 0, 1, or 2, provided that x+y+z+p=3.

Examples of radical $R^{31}$ include o-tolyl, o-ethylphenyl, o-n-propylphenyl, o-isopropylphenyl, o-n-butylphenyl, o-sec-butylphenyl, o-tert-butylphenyl, (o-phenyl)-phenyl, or 1-naphthyl groups.

Examples of radical $R^{32}$ include m-tolyl, m-ethylphenyl, m-n-propylphenyl, m-isopropylphenyl, m-n-butylphenyl, m-sec-butylphenyl, m-tert-butylphenyl, (m-phenyl)-phenyl, or 2-naphthyl groups.

Examples of radical $R^{33}$ include p-tolyl, p-ethylphenyl, p-n-propylphenyl, p-isopropylphenyl, p-n-butylphenyl, p-sec-butylphenyl, p-tert-butylphenyl, or (p-phenyl)-phenyl groups.

Radical $R^{34}$ may be, for example, phenyl, and p may be zero. The indices x, y, z, and p in compounds of Formula IVb may have the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |

-continued

| x | y | z | p |
|---|---|---|---|
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of Formula IVb are those in which p is zero, and $R^{31}$, $R^{32}$, and $R^{33}$ are independently selected from o-isopropylphenyl, m-tolyl, and p-tolyl, and $R^{34}$ is phenyl.

Additional examples of phosphites of Formula IVb are those in which $R^{31}$ is the o-isopropylphenyl radical, $R^{32}$ is the m-tolyl radical, and $R^{33}$ is the p-tolyl radical, with the indices listed in the above table; also those in which $R^{31}$ is the o-tolyl radical, $R^{32}$ is the m-tolyl radical, and $R^{33}$ is the p-tolyl radical, with the indices listed in the table; also those in which $R^{31}$ is the 1-naphthyl radical, $R^{32}$ is the m-tolyl radical, and $R^{33}$ is the p-tolyl radical, with the indices listed in the table; also those in which $R^{31}$ is the o-tolyl radical, $R^{32}$ is the 2-naphthyl radical, and $R^{33}$ is the p-tolyl radical, with the indices listed in the table; and lastly, those in which $R^{31}$ is the o-isopropylphenyl radical, $R^{32}$ is the 2-naphthyl radical, and $R^{33}$ is the p-tolyl radical, with the indices listed in the table; and mixtures of these phosphites.

In one embodiment, the catalyst precursor composition may comprise a zero-valent nickel, at least one multidentate P-containing ligand selected from the group consisting of a phosphite, a phosphonite, a phosphinite, a phosphine, and a mixed P-containing ligand or a combination of such members, and at least one monodentate P-containing ligand selected from tritolyl phosphite and phosphites of Formula IVb

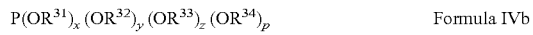

Formula IVb wherein $R^{31}$, $R^{32}$, and $R^{33}$ are independently selected from o-isopropylphenyl, m-tolyl, and p-tolyl, $R^{34}$ is phenyl, x is 1 or 2, and y, z, p are independently 0, 1, or 2, provided that x+y+z+p=3; and mixtures thereof.

A multidentate P-containing ligand may be suitable for use in the process of the invention if, as part of a catalyst precursor composition comprising a zero-valent nickel and the multidentate P-containing ligand, it can be used within a temperature range of about 80° C. to about 140° C., to produce a reaction mixture comprising 3PN and 2M3BN from a HCN-containing feed and a BD-containing feed. The multidentate P-containing ligand is suitable for use in the process of the invention in the case where the 2M3BN concentration of the reaction mixture comprising 3PN and 2M3BN can be maintained below about 15 weight percent of the total mass of the reaction mixture, for example at or below about 10 weight percent of the total mass of the reaction mixture, and the HCN conversion is about 95% or more. A catalyst precursor composition, comprising a P-containing ligand suitable for the process of the invention, may lack sufficient 3PN selectivity in BD hydrocyanation to produce a reaction mixture comprising 3PN and 2M3BN wherein the 2M3BN concentration is maintained below about 15 weight percent of the total mass of the reaction mixture. However, when used to hydrocyanate BD and to isomerize 2M3BN to 3PN concurrently in the same reaction zone, with a sufficient residence time, a catalyst precursor composition comprising a suitable P-containing ligand can produce a reaction mixture comprising 3PN and 2M3BN wherein the 2M3BN concentration is maintained below about 15 weight percent of the total mass of the reaction mixture. For the concurrent BD hydrocyanation/2M3BN isomerization process with a suitable multidentate P-containing ligand, the molar ratio of the HCN in the feed to the BD in the feed is in the range of about 0.90:1.00 to about 1.04:1.00. The molar ratio of the zero-valent nickel in the feed to the BD in the feed is in the range of about 0.00005:1.00 to about 0.0050:1.00. The mole ratio of multidentate P-containing ligand to zero-valent nickel is in the range of about 1/1 to about 6/1. Solvent, HCN, preparation of the catalyst precursor composition, reactor startup, and other operational information are as described for the process of the invention in other sections of this document.

The multidentate P-containing ligands useful in the catalyst precursor compositions employed in the present invention may be prepared by any suitable synthetic means known in the art, for example as described in at least some of the references cited as disclosing examples of multidentate P-containing ligands. For example, the multidentate P-containing ligands of Formula II and Formula III may be synthesized as described in U.S. Pat. Nos. 6,171,996 and 5,512,696, both of which are incorporated herein by reference. For example, the reaction of two equivalents of an ortho-substituted phenol with phosphorus trichloride gives the corresponding phosphorochloridite. The reaction of the phosphorochloridite with the desired substituted biphenol or octahydrobinaphthol in the presence of triethylamine gives the bidentate phosphite ligand. The crude bidentate phosphite ligand can be worked up by the process described in U.S. Pat. No. 6,069,267, which is incorporated herein by reference. As disclosed therein, the bidentate phosphite ligand product mixture can typically contain the desired product in about 70% to about 90% selectivity, with other phosphite by-products such as monodentate phosphites making up the balance of the product mixture. The bidentate phosphite ligand itself or these bidentate/monodentate phosphite ligand mixtures are suitable for use with the present invention.

The multidentate P-containing ligand itself or mixtures of the multidentate P-containing ligand and at least one monodentate P-containing ligand are suitable for use with the present invention.

The catalyst precursor compositions employed for this process should ideally be substantially free of carbon monoxide, oxygen, and water and may be preformed or prepared in situ according to techniques well known in the art. The catalyst precursor composition may be formed by contacting the multidentate P-containing ligand with a zero-valent nickel compound having ligands easily displaced by organophosphorus ligands, such as $Ni(COD)_2$, $Ni[P(O\text{-}o\text{-}C_6H_4CH_3)_3]_3$, and $Ni[P(O\text{-}o\text{-}C_6H_4CH_3)_3]_2(C_2H_4)$, all of which are well known in the art, wherein 1,5-cyclooctadiene (COD), tris(ortho-tolyl)phosphite [$P(O\text{-}o\text{-}C_6H_4CH_3)_3$], and ethylene ($C_2H_4$) are the easily displaced ligands. Elemental nickel, preferably nickel powder, when combined with a halogenated catalyst, as described in U.S. Pat. No. 3,903,120, is also a suitable source of zero-valent nickel. Alternatively, divalent nickel compounds can be combined with a reducing agent, to serve as a source of zero-valent nickel in the reaction, in the presence of the multidentate P-containing ligands. Suitable divalent nickel compounds include compounds of the formula $NiZ_2$ where Z is halide, carboxylate, or acetylacetonate. Suitable reducing agents include metal borohydrides, metal aluminum hydrides, metal alkyls, Li, Na, K, Zn, Fe or $H_2$. See, for example, U.S. Pat. No. 6,893,996. In the catalyst precursor composition, the multidentate P-containing ligand may be present in excess of what can theoretically be coordinated to the nickel at a given time.

The catalyst precursor composition may be dissolved in a solvent that is non-reactive toward, and miscible with, the hydrocyanation reaction mixture. Suitable solvents include, for example, aliphatic and aromatic hydrocarbons with 1 to 10 carbon atoms, and nitrile solvents such as acetonitrile. Alternatively, 3PN, a mixture of isomeric pentenenitriles, a mixture of isomeric methylbutenenitriles, a mixture of isomeric pentenenitriles and isomeric methylbutenenitriles, or the reaction product from a previous reaction campaign, may be used to dissolve the catalyst precursor composition.

The reaction temperature is maintained within the range of about 80° C. to about 140° C., for example within the range of about 100° C. to about 130° C. Generally, the reaction pressure should be sufficient to maintain the reagents in the liquid state, with such pressure at least, in part, a function of the amount of unreacted BD present in the reaction mixture. Though the invention is not limited by an upper limit of pressure, for practical purposes the pressure generally ranges from about 15 psia to about 300 psia (about 103 kPa to about 2068 kPa).

HCN, substantially free of carbon monoxide, oxygen, ammonia, and water can be introduced to the reaction as a vapor, liquid, or mixtures thereof. As an alternative, a cyanohydrin can be used as the source of HCN. See, for example, U.S. Pat. No. 3,655,723.

The molar ratio of the HCN in the feed to the BD in the feed is in the range of about 0.90:1.00 to about 1.04:1.00, for example in the range of about 0.92:1.00 to about 0.98:1.00. Avoiding the use of a large excess of BD in relation to HCN can be advantageous in that, after reaction, the small quantity of unreacted BD may not warrant recovery and recycle to the hydrocyanation reactor. Additionally, the formation of thermally-driven BD-based yield loss products, such as BD dimers, can be reduced with lower BD amounts.

The molar ratio of the zero-valent nickel in the feed to the BD in the feed is in the range of about 0.00005:1.00 to about 0.0050:1.00, for example in the range about 0.0001:1.00 to about 0.0010:1.00.

The residence time in the reaction zone (for example, the time necessary for the combined feeds to displace one reactor volume in a CSTR) is typically determined by the desire to maintain the 2M3BN concentration below about 15 weight percent of the reaction mass, for example at or below about 10 weight percent of the reaction mass, and is also related to the catalyst concentration and reaction temperature. Generally residence times will be in the range of about 0.5 to about 15 hours, for example in the range of about 1 to about 10 hours.

The hydrocyanation and isomerization reaction mixture may be used "as is" in subsequent reaction steps for the production of ADN. Alternatively, the reaction product and components of the catalyst precursor composition can be recovered by conventional techniques known in the art, such as, for example, by liquid-liquid extraction as disclosed in U.S. Pat. No. 6,936,171 and by flash distillation, for example at a pressure in the range of about 10 torr to about 700 torr (about 1 kPa to about 93 kPa). The catalyst precursor composition-containing "distillation tails" may be recycled back to the reaction zone after purging a portion of the mixture to prevent build-up of "high boiling" impurities. The reaction product, the "distillation make", is a mixture comprised predominantly of 3PN, with lesser amounts of isomeric pentenenitriles, 2M3BN, 2-methyl-2-butenenitrile, BD, HCN, and vinylcyclohexene. The desired 3PN and other isomeric pentenenitriles can be recovered from the reaction product by distillation and other constituent parts such as BD, HCN, and 2M3BN either recycled to the reaction zone or disposed of.

The following Examples were performed using a catalyst precursor composition wherein the multidentate P-containing ligand was a bidentate P-containing ligand, referred to as "Phosphite A" in the chemical formula for the nickel source below. The multidentate P-containing ligand of the Examples is represented by Formula II wherein $R_1$ is isopropyl; $R_2$, $R_6$, and $R_8$ are H; and $R_3$, $R_4$, $R_5$, and $R_7$ are methyl. The nickel source charged to the autoclave comprised the compound (Phosphite A)Ni(crotyl)CN dissolved in a nitrile solvent mixture. "Crotyl" represents a butenyl group having the empirical formula $C_4H_7$.

The multidentate P-containing ligand, Phosphite A, of the Examples may be prepared by any suitable synthetic means known in the art. For example, 3,3'-diisopropyl-5,5',6,6'-tetramethyl-2,2'-biphenol can be prepared by the procedure disclosed in United States Published Patent Application No. 2003/0100802, which is incorporated herein by reference, in which 4-methylthymol can undergo oxidative coupling to the substituted biphenol in the presence of a copper chlorohydroxide-TMEDA complex (TMEDA is N,N,N',N'-tetramethylethylenediamine) and air.

The phosphorochloridite of 2,4-xylenol, $(C_8H_9O)_2PCl$, can be prepared, for example, by the procedure disclosed in United States Published Patent Application No. 2004/0106815, which is incorporated herein by reference. To form this phosphorochloridite selectively, anhydrous triethylamine and 2,4-xylenol can be added separately and concurrently in a controlled manner to $PCl_3$ dissolved in an appropriate solvent under temperature-controlled conditions.

The reaction of the phosphorochloridite with the 3,3'-diisopropyl-5,5',6,6'-tetramethyl-2,2'-biphenol to form the desired multidentate P-containing ligand, Phosphite A, can be performed, for example, according to the method disclosed in U.S. Pat. No. 6,069,267, which is hereby incorporated by reference. The phosphorochloridite can be reacted with 3,3'-diisopropyl-5,5',6,6'-tetramethyl-2,2'-biphenol in the presence of an organic base to form Phosphite A, which can be isolated according to techniques well known in the art, as also described in U.S. Pat. No. 6,069,267.

For each Example, the (Phosphite A)Ni(crotyl)CN compound was prepared as follows. In a nitrogen atmosphere, the Phosphite A, represented by Formula II wherein $R_1$ is isopropyl; $R_2$, $R_6$, and $R_8$ are H; and $R_3$, $R_4$, $R_5$, and $R_7$ are methyl, and $Ni(COD)_2$ (COD is 1,5-cyclooctadiene) were combined in a molar ratio of 1:11 in a flask. Trans-3-pentenenitrile (95 wt %, Aldrich), which had been previously dried over molecular sieves and degassed with nitrogen, was added to the same flask (about 200 mL for 10 g of Phosphite A) and the mixture was stirred until an orange homogeneous solution formed. All volatiles were removed under vacuum at ambient temperature to yield an orange powder. The powder was triturated with anhydrous acetonitrile to remove excess pentenenitriles and other impurities, and then all volatiles were again removed under vacuum to produce (Phosphite A)Ni(crotyl)CN as an orange solid.

Trans-3-pentenenitrile (95 wt %) produced from BD hydrocyanation, 2M3BN isomerization, and pentenenitrile hydrocyanation processes may be obtained commercially from the Sigma-Aldrich Chemical Company. This material contains trace amounts of 2M3BN also prepared from a BD hydrocyanation and/or 2M3BN isomerization process.

The purity of the BD feed was greater than 99%. Freshly prepared anhydrous, uninhibited, liquid HCN was utilized in all Examples.

Embodiments falling within the scope of the present invention may be further understood in view of the following non-limiting examples.

EXAMPLES

Example 1

The reaction was carried out in a 100 mL autoclave fitted with a magnetically driven stirrer and dip legs for the addition of feeds. The reactor was operated liquid full, which resulted in a working volume of 118 mL. The reaction temperature was maintained at 120° C. by means of a combination of electrical heating on the outside and passing coolant through an internal coil. Pressure in the reactor was controlled by a manual back-pressure regulator at 130 psia (896 kPa). The exit tube continuously fed a flash-distillation column, which operated under reduced pressure (100 torr; 13.3 kPa) to separate reaction products from the catalyst.

A catalyst precursor composition solution comprised of (Phosphite A)Ni(crotyl)CN (2.5 wt %), 1.6 wt % Phosphite A, and 1.2 wt % Phosphite A oxides, 3PN (82 wt %), 2PN (0.9 wt %), 4PN (1.2 wt %), 2M3BN (1.4 wt %), 2-methyl-2-butenenitriles (2M2BN, 0.7 wt %), dimethylsuccinonitrile (1.0 wt %), MGN (3.5 wt %), and ADN (2.4 wt %), was fed continuously and concurrently with BD and HCN to the autoclave such that the molar ratio of Ni:HCN:BD fed was about 0.00046:0.963:1.0 and the total flow rates were such that the residence time in the reactor was about 3.4 hours. Flows were maintained for 24 hours in order to approach a steady state condition. Samples were periodically drawn from the line exiting the reactor and analyzed by both high-pressure liquid chromatography (HPLC) for catalyst and by gas chromatography (GC) for nitrile products and byproducts. The 2M3BN was analyzed at 6.6 wt % of the reaction mixture. 92.9% of the BD and 96.5% of the HCN fed to the autoclave was converted into useful products comprised of 2PN, 3PN, 4PN, and 2M3BN. Of the total moles of BD converted, the selectivity to these useful products was 96.7%.

Example 2

The reaction was carried out in a 1 liter autoclave fitted with a magnetically driven stirrer and dip legs for the addition of feeds and removal of product. The product removal dip leg was adjusted to provide a working volume of 750 mL. The reaction temperature was maintained at 110° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00055:0.946:1.0 and the total flow rates were such that the residence time in the reactor was about 7.3 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 6.6 wt % of the reaction mixture. 91.1% of the BD and 96.3% of the HCN fed to the autoclave was converted into useful products comprised of 2PN, 3PN, 4PN, and 2M3BN. Of the total moles of BD converted, the selectivity to these useful products was 96.1%.

Example 3

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 120° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00025:0.948:1.0 and the total flow rates were such that the residence time in the reactor was about 8.2 hours. Flows were maintained for 40 hours in order to approach a steady state condition. Samples were periodically drawn from the line exiting the reactor and analyzed by both HPLC for catalyst and by GC for nitrile products and byproducts. The 2M3BN was analyzed at 10.3 wt % of the reaction mixture. 90.9% of the BD and 96.9% of the HCN fed to the autoclave was converted into useful products comprised of 2PN, 3PN, 4PN, and 2M3BN. Of the total moles of BD converted, the selectivity to these useful products was 96.5%.

Example 4

The reaction was carried out in a 1 liter autoclave fitted with a magnetically driven stirrer and dip legs for the addition of feeds and extraction of product. The product removal dip leg was adjusted to provide a working volume of 750 mL. The reaction temperature was maintained at 130° C. by means of a combination of electrical heating on the outside and passing coolant through an internal coil. Pressure in the reactor was controlled by a manual back-pressure regulator at 100 psia (689 kPa). The exit tube continuously fed a flash-distillation column, which operated under reduced pressure (300 torr; 40 kPa) to separate reaction products from the catalyst.

A catalyst precursor composition solution comprised of (Phosphite A)Ni(crotyl)CN (2.8 wt %), 2.1 wt % Phosphite A, and 1.4 wt % Phosphite A oxides, 3PN (83 wt %), 2PN (6.1 wt %), 4PN (0.8 wt %), 2M3BN (1.4 wt %), 2M2BN (0.9 wt %), dimethylsuccinonitrile (1.0 wt %), MGN (0.2 wt %), and ADN (1.7 wt %), was fed continuously and concurrently with BD and HCN to the autoclave such that the molar ratio of Ni:HCN:BD fed was about 0.00035:0.925:1.0 and the total flow rates were such that the residence time in the reactor was about 2.0 hours. Flows were maintained for 12 hours in order to approach a steady state condition. Samples were periodically drawn from the line exiting the reactor and analyzed by both HPLC for catalyst and by GC for nitrile products and byproducts. The 2M3BN was analyzed at 12.4 wt % of the reaction mixture. 89.1% of the BD and 96.3% of the HCN fed to the autoclave was converted into useful products comprised of 2PN, 3PN, 4PN, and 2M3BN. Of the total moles of BD converted, the selectivity to these useful products was 96.7%.

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for the continuous production of 3-pentenenitrile, comprising:
    (a) continuously introducing feed comprising hydrogen cyanide, 1,3-butadiene, and a catalyst precursor composition to a reaction zone, wherein the molar ratio of the hydrogen cyanide in the feed to the 1,3-butadiene in the feed is in the range of about 0.90:1.00 to about 1.04:1.00, and wherein the catalyst precursor composition comprises a zero-valent nickel and at least one multidentate phosphorus-containing ligand selected from the group consisting of a phosphite, a phosphonite, a phosphinite, a phosphine, and a mixed phosphorus-containing ligand or a combination of such members;
    (b) displacing a product mixture from the reaction zone by the feed which is continuously introduced into the reaction zone; and
    (c) maintaining a residence time in the reaction zone sufficient to convert about 95% or more of the hydrogen cyanide and to produce the product mixture, wherein the product mixture comprises 3-pentenenitrile and 2-methyl-3-butenenitrile, and wherein the 2-methyl-3-butenenitrile concentration is maintained below about 15 weight percent of the total mass of the product mixture.

2. The process according to claim 1, wherein the molar ratio of the zero-valent nickel in the feed to the 1,3-butadiene in the feed is in the range of about 0.00005:1.00 to about 0.0050:1.00.

3. The process according to claim 1, wherein the temperature is maintained within a range of about 80° C. to about 140° C.

4. The process according to claim 1, wherein the multidentate phosphorus-containing ligand is a phosphite.

5. The process according to claim 1, wherein the multidentate phosphorus-containing ligand is a phosphonite.

6. The process according to claim 1, wherein the multidentate phosphorus-containing ligand is a phosphinite.

7. The process according to claim 1, wherein the multidentate phosphorus-containing ligand is a phosphine.

8. The process according to claim 1, wherein the multidentate phosphorus-containing ligand is a mixed phosphorus-containing ligand comprising at least one combination selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

9. The process according to claim 1, wherein the temperature is maintained within the range of about 100° C. to about 130° C.

10. The process according to claim 1, wherein the molar ratio of the hydrogen cyanide in the feed to the butadiene in the feed is in the range of about 0.92:1.00 to about 0.98:1.00.

11. The process according to claim 1, wherein the molar ratio of the zero-valent nickel in the feed to the butadiene in the feed is in the range of about 0.0001:1.00 to about 0.0010:1.00.

12. The process according to claim 1, wherein the residence time in the reaction zone is sufficient to maintain the 2-methyl-3-butenenitrile concentration at or below about 10 weight percent of the total mass of the product mixture.

13. The process according to claim 1, wherein said feed comprises 2-methyl-3-butenenitrile.

14. The process according to claim 1, wherein the catalyst precursor composition further comprises at least one monodentate phosphorus-containing ligand selected from the group consisting of a phosphite, a phosphonite, a phosphinite, and a phosphine or a combination of such members.

15. The process according to claim 1, wherein the multidentate phosphorus-containing ligand is a bidentate phosphite.

16. The process according to claim 1, wherein the multidentate phosphorus-containing ligand is a bidentate phosphonite.

17. The process according to claim 1, wherein the multidentate phosphorus-containing ligand is a bidentate phosphinite.

18. The process according to claim 1, wherein the multidentate phosphorus-containing ligand is a bidentate phosphine.

19. The process according to claim 1, wherein the multidentate phosphorus-containing ligand is a bidentate mixed phosphorus-containing ligand selected from the group consisting of a phosphite-phosphonite, a phosphite-phosphinite, a phosphite-phosphine, a phosphonite-phosphinite, a phosphonite-phosphine, and a phosphinite-phosphine or a combination of such members.

* * * * *